Figure 1:
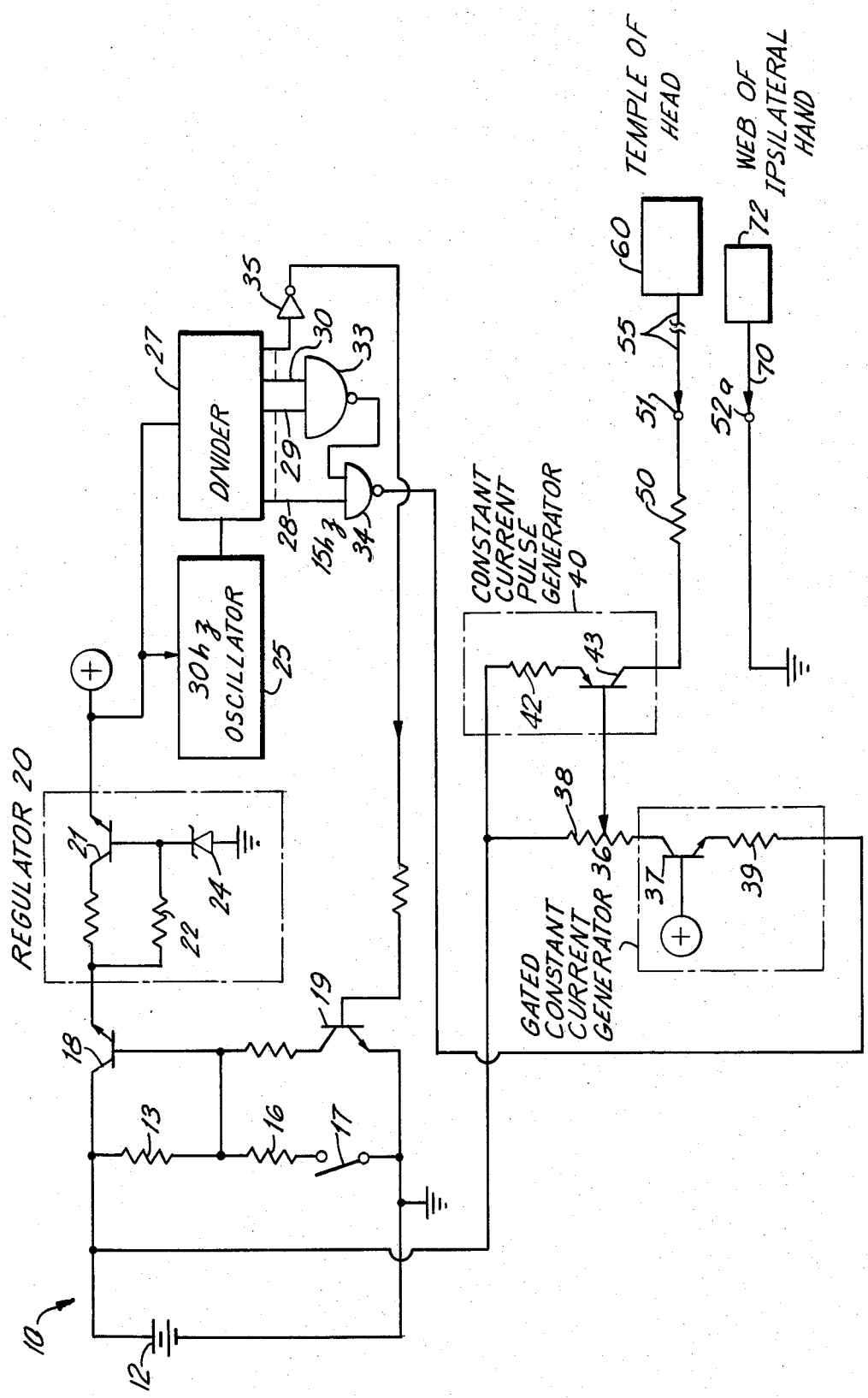

United States Patent [19]

Liss et al.

[11] Patent Number: 4,614,193
[45] Date of Patent: * Sep. 30, 1986

[54] ELECTRONIC GLAUCOMA TREATMENT APPARATUS AND METHODOLOGY

[75] Inventors: Saul Liss; Bernard Liss, both of Glen Rock, N.J.

[73] Assignee: Pain Suppression Labs, Inc., Elmwood Park, N.J.

[*] Notice: The portion of the term of this patent subsequent to Nov. 5, 2002 has been disclaimed.

[21] Appl. No.: 618,144

[22] Filed: Jun. 7, 1984

Related U.S. Application Data

[63] Continuation-in-part of Ser. No. 569,476, Jan. 9, 1984, Pat. No. 4,550,733.

[51] Int. Cl.⁴ ............................................... A61N 1/34
[52] U.S. Cl. ................................................ 128/419 R
[58] Field of Search .................... 128/419 R, 421–423, 128/793

[56] References Cited

U.S. PATENT DOCUMENTS

| | | | |
|---|---|---|---|
| 2,004,751 | 6/1935 | Fischer et al. | 128/423 R |
| 3,640,284 | 2/1972 | DeLangis | 128/422 |
| 3,791,373 | 2/1974 | Winkler et al. | 128/422 |
| 3,902,502 | 9/1975 | Liss et al. | 128/422 |
| 4,155,366 | 5/1979 | DiMucci | 128/421 |
| 4,271,841 | 6/1981 | Friedman | 128/419 R |
| 4,305,402 | 12/1981 | Katims | 128/421 |
| 4,503,863 | 3/1985 | Katims | 128/421 |

FOREIGN PATENT DOCUMENTS

| | | | |
|---|---|---|---|
| 2500309 | 8/1982 | France | 128/422 |
| 605603 | 5/1978 | U.S.S.R. | 128/421 |

*Primary Examiner*—William E. Kamm
*Assistant Examiner*—Mitchell J. Shein
*Attorney, Agent, or Firm*—Hopgood, Calimafde, Kalil, Blaustein & Judlowe

[57] ABSTRACT

Glaucoma treatment apparatus and methodology employs a transcutaneous electronic wave to suppress pain and reduce intra-ocular pressure. A first positive contact electrode is placed at the temple of the head, and a second negative contact electrode is placed at the web of the ipsilateral hand. An electronic current wave comprising relatively high frequency pulses with a low frequency amplitude modulation is then applied between the first to the second electrodes.

3 Claims, 5 Drawing Figures

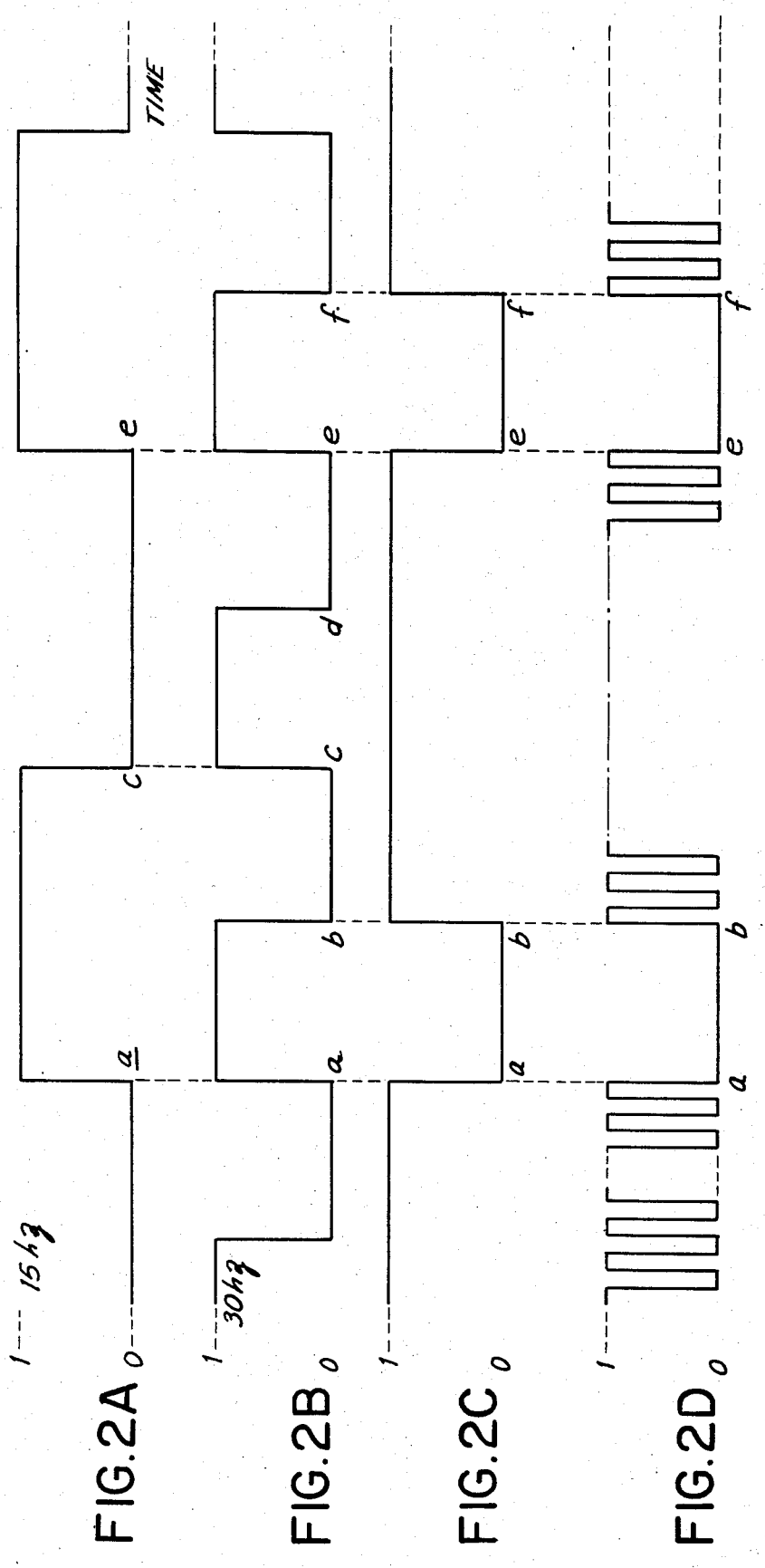

ELECTRONIC GLAUCOMA TREATMENT APPARATUS AND METHODOLOGY

This application is a continuation-in-part of U.S. application Ser. No. 569,476 filed Jan. 9, 1984, U.S. Pat. No. 4,550,733.

DISCLOSURE OF THE INVENTION

This invention relates to medical electronic apparatus and methodology and, more specifically, to glaucoma treatment apparatus and procedure for treating symptoms incident to the disease.

It is an object of the present invention to provide improved glaucoma treatment apparatus and methodology.

More specifically, an object of the present invention is the electronic treatment of glaucoma in a safe, efficient and rapid manner to reduce intra-ocular pressure and alleviate pain associated with the disease.

It is a further object of the present invention to provide electronic transcutaneous electronic nerve stimulating equipment operative at very low, milliampere current levels, which relieves perceived pain, and treats the symptoms of glaucoma.

The above and other objects and features of the instant invention are realized in a specific illustrative glaucoma electronic treatment apparatus and methodology which employs a transcutaneous electronic wave to suppress perceived pain as well as all other symptoms associated with glaucoma. A first, positive electrode is placed at the temple of the patient's head, with a negative, second electrode disposed at the web of the ipsilateral hand. An electronic current wave comprising relatively high frequency pulses with a low frequency modulation is then applied from the first to the second electrode.

The above and other features and advantages of the instant invention will become more clear from the following detailed description of a specific illustrative embodiment thereof, presented hereinbelow in conjunction with the accompanying drawing, in which:

FIG. 1 is a schematic diagram of electronic glaucoma treatment apparatus embodying the principles of the present invention; and FIGS. 2A through 2D are wave forms illustrating the operation of the FIG. 1 apparatus.

The term "glaucoma" indicates that the pressure inside an eye is raised. It covers several conditions characterized by a raised intra-ocular tension, all of which may end in the same state of absolute glaucoma with a totally blind and often extremely painful eye. The diagnostic features are an intra-ocular pressure greater than 21 mm Hg, enlargement of the optic cup, and visual field loss.

Several theories as to the cause of the disease have been suggested. A common mistake is to regard chronic simple glaucoma as a purely "eye" disease and to try to explain it on mechanical grounds of secretion/drainage imbalance. Certainly, changes do occur in the constituent parts of the angle of the anterior chamber with increasing age. There are, for instance, changes in the collagen and mucopolysaccharides of the trabecular meshwork and the exit channels and, particularly, the inner trabecular wall of the canal of Schlemm become thickened, all of which could lead to impairment of the drainage facility. Gamma globulins and plasma cells have been shown in the trabecular areas in eyes of patients with chronic simple glaucoma, at least raising the possibility of an immunological element in the aetiology. An abnormal glucose tolerance occurs in a high percentage of glaucoma and pre-glaucoma subjects as it does in diabetes mellitus, and diabetics seem to be particularly susceptible to develop glaucomatous field defects. A low protein bound iodine plasma level characterizes both glaucoma and hypothyroidism. Glaucoma and pre-glaucoma subjects are "non-tasters" with phenylthiocarbamide. Affecting the older age group which it most often does, glaucoma is often associated with arteriosclerosis and vascular hypertension. There does not seem to be any direct relationship between intra-ocular pressure and blood pressure and these conditions along with such diseases as carotid insufficiency and blood loss are more easily correlated with the condition once known as "low tension glaucoma" but now referred to as ischaemic optic neuropathy. It might be expected that atmospheric pressure would exert an influence on the intra-ocular pressure, as both "push" on opposite sides of the cornea. In fact, changes in atmospheric pressure seem to have little or no effect on intra-ocular pressure, normal or raised.

It is usually only in the diagnosis of chronic simple glaucoma that difficulty arises. The other types are characterized by pain and redness of the eye and with marked and sudden impairment of vision, symptoms which the patient will not ignore. In addition, there will be evidence of other eye trouble in the case of secondary glaucoma, and the angle of the anterior chamber will be seen (with a gonioscope) to be closed in closed angle glaucoma. Some subacute attacks of angle closure glaucoma do occur and settle spontaneously; these cause headache and blurring of vision lasting perhaps an hour or two and a very suggestive symptom of these attacks is that during them the patient sees rainbow-colored rings around white lights.

In angle closure glaucoma the immediate cause of the rise in pressure within the eye is a failure of the aqueous fluid to drain satisfactorily through the pupil, causing the iris to balloon forwards and mechanically block the drainage angle. This leads to a vicious circle as the rising pressure pushes the iris more firmly into the angle. See R. J. McWilliam "Glaucoma" *Scot.Med.J.* 1978, 23:286 the disclosure of which is incorporated by reference.

The apparatus of the instant invention has been found to relieve the symptoms of glaucoma with a relatively low level current and without chemical intervention.

The apparatus of FIG. 1 is utilized to treat the symptoms associated with the diseased state of a patient who is suffering from glaucoma. A first positive contact electrode 60 (FIG. 1) is placed on the temple of the head. A second negative contact electrode 72 (FIG. 1) is placed at the web of the ipsilateral hand. The treatments should be for 10 minutes and may be run concurrently.

An electronic wave (depicted in FIG. 2D) is applied between the first electrode 60, and the electrode 72 which are connected on common. The wave form of FIG. 2D comprises a low level (less than 4 milliamperes) pulse train of relatively high frequency, e.g., between 12 and 20 khz modulated in amplitude by a relatively low frequency wave in the range of 8 to 20 hz. The low frequency wave is preferably non-symmetrical (that shown in FIG. 2D), for example, characterized by a 3:1 duty cycle, being on three quarters of the time and off one quarter of the recurring period. For concreteness only and without limitation, it will hereinafter be assumed that the high frequency pulse occurs at a 15 khz rate and 1-1.5 m.a. level, while being subject to a 15 hz modulation with a 3:1 duty factor.

I have found that the wave of FIG. 2D is effective to block the pain perceived and relieve the symptoms associated with glaucoma. One can see a gradual decline in the patient's intra-ocular pressure which is accompanied by alleviation of pain.

The particular mechanism causing elimination of the intra-ocular pressure is believed to follow from some alleviation of the mechanical blockage in the drainage mechanism which is responsive to the low frequency modulation envelope introduced into the body, with the high frequency wave constituent serving as a transcutaneous carrier for the low frequency modulation, thereby allowing the aqueous fluid to drain satisfactorily through the pupil.

While the precise operative mechanism may be the subject of debate, the fact of the relief of pain and reduction of intra-ocular pressure produced by the instant invention is not.

The FIG. 1 electronic apparatus 10 for generating and applying the wave form of FIG. 2D will now be specifically considered. A battery 12 is connected to a PNP series pass transistor 18 which, in turn, selectively passes the voltage from battery 12 through a voltage regulator 20 to form the positive direct current voltage supply for the apparatus 10 electronics. The unit is first turned on by momentarily closing a power-on switch 17. This applies a low voltage to the base of PNP transistor 18, turning that device on and effectively coupling the potential of battery 12 to a series pass transistor 21 in the voltage regulator 20. Because the final output of a counter or divider chain 27 is initially low on power turn on, the resulting high output of inverter 35 applies a high potential to the base of transistor 19, turning it on and thereby latching PNP transistor 18 to its conductive condition when switch 17 is released. This maintains the electronic apparatus on for a desired period which is determined by the frequency of an oscillator 25 and the division factor of the divider 27, i.e., the period required for the most significant stage of the counter 27 to reach its high or binary "1" state. The switched power supply assures that the electronic apparatus is not inadvertently left on to unduly discharge the battery 12.

The regulated output of battery 12 applied through PNP transistor 18 is converted to a lower regulated value by the regulator 20. Regulator 20 is per se well known and includes the series pass NPN transistor 21 having a constant voltage applied to the base thereof by a Zener diode 24 energized by a resistor 22. The constant potential output of regulator 20, which serves as the supply voltage for much of the remaining electronics of FIG. 1, is the characteristic reverse excitation voltage of Zener diode 24 less about 7/10 of a volt for the base-emitter drop of transistor 21.

As above noted, the active power supply interval for circuit 10 of the drawing is fixed and preset to a specific period. The above-discussed time out circuitry is employed to assure that the unit is not inadvertently left on. Many ways of achieving this result will be readily apparent to those skilled in the art. For example, a variable time out may be provided by employing a switch to connect the input of inverter 35 to varying ones of the more significant stage outputs of the pulse counter chain 27. Yet further, separate electronic or electromechanical timer apparatus, fixed or variable, all per se well known, may be employed to supply a positive potential to the base of transistor 19 for the desired "on" period; and to switch off the base drive to transistor 19, thereby turning off series pass transistor 18, when the desired operative period has passed.

A time base oscillator 25 supplies an input to the pulse counter or divider chain 27. The frequency of oscillator 25 is chosen for convenience to be an integral multiple of the pulse frequency (FIG. 2D) desired for delivery to the patient. For the assumed 15 khz desired frequency, a 30 khz oscillation repetition rate may be usefully employed for oscillator 25, such that the 15 khz signal is derived at a divide-by-two tap 28 of divider chain 27. The 15 khz signal is supplied as one input to a NAND gate 34, the output of which corresponds to the ultimately desired wave of FIG. 2D. Outputs 29 and 30 of divider 27 are supplied as inputs to a NAND gate 33, the output of which is supplied as a second input to the NAND gate 34. The output 29 of divider 27 supplies the 30 hz wave of FIG. 2B (pulse division factor 1,000 at tap 29), while the 15 hz wave of FIG. 2A is supplied at a divider output 30 (divider factor: 2,000). Logic gate 33 generates the output wave of FIG. 2C, being at its high or Boolean "1" value when either of the waves of FIGS. 2A or 2B is low (i.e., preceding the time a, during the interval b-e, - and following time f). Correspondingly, during the periods a-b and e-f when the output at divider 27 taps 29 and 30 are both high, the output of gate 33 is low (Boolean "0" value).

The wave form of FIG. 2C is supplied as one input to the gate 34 together with the 15 khz pulse train at the divide-by-two counter 27 output port 28. Accordingly, the output of NAND gate 34 switches between its high and low state during the periods when the FIG. 2C wave is high, i.e., preceding time a, during the interval b-e, following the time f, and so forth for the recurring pattern illustrated by FIGS. 2A-2D.

The voltage wave form of FIG. 2D is converted to a current in the milliampere range for application to the patient by the following circuitry of FIG. 1. As a first matter, a gated constant current generator 36 passes a gated current (either off or of a fixed value) through a potentiometer 38 under control of the output of the NAND gate 34. When the output of NAND gate is low, a transistor 37 in constant current generator 36 is on and a current substantially given by the positive potential output of regulator 20 (applied to the base of transistor 37) less a 7/10 of a volt base emitter drop for the transistor 37, divided by the resistance value of the resistance 39 in the emitter circuit of transistor 37. The voltage at the variable tap of the potentiometer 38 is supplied to the base of a PNP transistor 43 of a constant current pulse generator 40. The output of pulse generator 40 is a current which switches between its off (zero current) state, and a value given by the voltage at the potentiometer 38 tap, less a diode drop for the emitter-base of transistor 43, divided by the resistance value of resistor 42 connected in the emitter circuit of the PNP device 43. This pulsed current output of pulse generator 40 corresponds in wave form to FIG. 2D, and is at a level, determined by the setting of potentiometer 38, in the low milliampere range. It is this current pulse which is ultimately delivered to the patient to provide the requisite relief of symptoms.

The current pulses from generator 40 pass through a protective, series limiting resistor 50 to an output terminal 51. It there flows via the lead 55 connected to terminal 51 to the electrode 60 adhered to the patient's temple. The current transcutaneously passes into the patient, flows through the patient, and returns to electronic ground via the electrode pad 72 adhered to the web of the patient's ipsilateral hand. Electrode 72 is connected to electronic system ground via lead 70 and apparatus terminal port 52a.

As above noted, the apparatus and methodology of the instant invention treats the intra-ocular pressure and other symptoms associated with glaucoma. The apparatus and methodology has manifest advantages for alleviating the patient's symptoms.

EXAMPLES

A group of patients were treated by the apparatus and methodology of the instant invention for a period of ten minutes. Their intra-ocular pressure was measured prior to treatment (To), shortly after treatment (Tpost), between two and three hours after treatment (T2-3), between five and six hours after treatment (T5-6), and between seven and eight hours after treatment (T7-8). Only one eye of each subject was treated, that eye being indicated by the right (R) or left (L) indication following the patient designation in the "treated" column below. Measurements on the untreated eye are as indicated in the "untreated" portion of the table below. The results of the testing is as follows:

|  | To | Tpost | T2-3 | T5-6 | T7-8 |
|---|---|---|---|---|---|
| Treated |  |  |  |  |  |
| A (R) | 28 | 26 | 26 | 23 | 22 |
| B (R) | 30 | 30 | 25 | 26 | 22 |
| C (L) | 26 | 26 | 24 | 22 | 24 |
| D (R) | 26 | 23 | 24 | 23 | 22 |
| E (L) | 46 | 44 | 45 | 38 | 36 |
| F (R) | 34 | 32 | 33 | 30 | 30 |
| Average | 31.7 | 30.2 | 29.5 | 27 | 26.5 |
| Untreated |  |  |  |  |  |
| A (L) | 28 | 26 | 26 | 23 | 22 |
| B (L) | 30 | 30 | 25 | 26 | 22 |
| C (R) | 25 | 26 | 22 | 22 | 21 |
| D (L) | 31 | 29 | 30 | 30 | 29 |
| E (R) | 51 | 51 | 53 | 48 | 48 |
| F (L) | 37 | 36 | 36 | 33 | 38 |
| Average | 33.7 | 33 | 32 | 30.3 | 30 |

The above data demonstrates reduction in intra-ocular pressure immediately following completion of treatment. Moreover, for substantial periods following treatment, the pressure continues to decrease, alleviating the greater part of the overpressure in the preponderance of patients treated. Moreover, some benefit is also realized in the untreated eye. The computer data is as follows:

| GLAUCOMA INTRA-OCULAR PRESSURE REDUCTION ANALYSIS | | | | |
|---|---|---|---|---|
| Maximum Reading | Minimum Reading | Difference | Maximum Rdg. Active Range | Percentage Decrease |
| Treated | | | | |
| A (R) 28 | 22 | 6 | 18 | 33.3 |
| B (R) 30 | 22 | 8 | 20 | 40 |
| C (L) 26 | 22 | 4 | 16 | 25 |
| D (R) 26 | 22 | 4 | 16 | 25 |
| E (L) 46 | 36 | 10 | 36 | 27.8 |
| F (R) 34 | 30 | 4 | 24 | 16.7 |
| Average 31.7 | 26.5 | 5.2 | 21.7 | 27.9 |
| Untreated | | | | |
| A (L) 28 | 22 | 6 | 18 | 33.3 |
| B (L) 30 | 22 | 8 | 20 | 40 |
| C (R) 26 | 21 | 5 | 16 | 31.3 |
| D (L) 31 | 29 | 2 | 21 | 9.5 |
| E (R) 53 | 48 | 5 | 43 | 11.6 |
| F (L) 38 | 33 | 5 | 28 | 17.9 |
| Average 33.7 | 30 | 3.7 | 23.7 | 23.9 |

The above-described arrangement and methodology are merely illustrative of the principles of the present invention. Numerous modifications and adaptations thereof will be readily apparent to those skilled in the art without departing from the spirit and scope of the present invention.

What is claimed is:

1. A method for suppressing pain and reducing intra-ocular pressure associated with the disease glaucoma including the steps of securing a first electrode on the temple of the head, securing a second electrode to the web of the subject's ipsilateral hand, and supplying an electrical wave comprising a high frequency amplitude modulation to said first and said second electrodes.

2. The method as in claim 1, wherein the frequency of said high frequency electrical wave was in the range of 12-20 khz, wherein said low frequency modulation is in the range 8-20 hz, and wherein said wave does not exceed about 4 milliamperes.

3. The method as in claim 1, wherein said amplitude modulation is non-symmetrical.

* * * * *